United States Patent [19]

Vecchietti et al.

[11] Patent Number: 5,089,507
[45] Date of Patent: Feb. 18, 1992

[54] HETEROCYCLIC PIPERIDINYL COMPOUNDS HAVING ANALGESIC EFFECT

[75] Inventors: Vittorio Vecchietti; Roberto Colle, both of Milan; Antonio Giordani, Pavia; Giulio Dondio, Milan, all of Italy

[73] Assignee: Dr. L. Zambeletti SpA, Italy

[21] Appl. No.: 412,133

[22] Filed: Sep. 25, 1989

[30] Foreign Application Priority Data

Sep. 26, 1988 [GB] United Kingdom ............... 8822508
Jul. 18, 1989 [GB] United Kingdom ............... 8916396

[51] Int. Cl.⁵ ............... A61K 31/445; C07D 401/14; C07D 417/14; C07D 211/06
[52] U.S. Cl. ............... 514/326; 514/212; 514/222.2; 514/227.8; 514/235.5; 514/317; 514/318; 514/319; 514/320; 514/321; 514/323; 514/324; 514/330; 540/481; 540/484; 540/476; 540/544; 544/60; 544/130; 546/139; 546/143; 546/146; 546/195; 546/196; 546/197; 546/198; 546/200; 546/205; 546/206; 546/208; 546/209; 546/226; 546/227
[58] Field of Search ............ 540/476, 544, 481, 48.4; 514/212, 227.8, 235.5, 222.2, 317, 318, 319, 320, 321, 324, 323, 326, 330; 544/60, 130; 546/139, 195, 196, 197, 200, 201, 205, 208, 209, 226, 227, 143, 146, 198, 206

[56] References Cited

U.S. PATENT DOCUMENTS 4,801,585  1/1989  Vecchietti et al. ............... 546/208
4,826,819  5/1989  Vecchietti et al. ............... 546/208

FOREIGN PATENT DOCUMENTS 330467  8/1989  European Pat. Off. .
333315  9/1989  European Pat. Off. .

*Primary Examiner*—Jane T. Fan
*Assistant Examiner*—Celia Chang
*Attorney, Agent, or Firm*—Rosenman & Colin

[57] ABSTRACT

A compound, or a solvate or salt thereof, of formula (I):

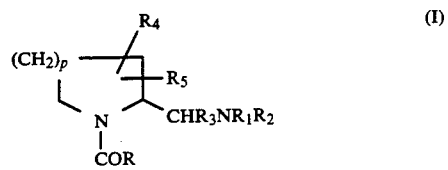

in which:
RCO is an acyl group in which the group R contains a substituted or unsubstituted carbocyclic aromatic or heterocyclic aromatic ring;
$R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups, or together form a $C_{2-8}$ branched or linear polymethylene or $C_{2-6}$ alkenylene group, optionally substituted with a hetero-atom,
$R_3$ is hydrogen, $C_{1-6}$ alkyl or phenyl, or $R_3$ together with $R_1$ form a $-(CH_2)_3-$ or $-(CH_2)_4-$ group;
$R_4$ and $R_5$ are independently hydrogen, hydroxyl, halogen, $C_{1-6}$ alkyl or aryl, provided both $R_4$ and $R_5$ are not simultaneously hydrogen; and p is an integer from 1 to 4,
is useful for the treatment of pain or hyponatraemic disease states.

7 Claims, No Drawings

HETEROCYCLIC PIPERIDINYL COMPOUNDS HAVING ANALGESIC EFFECT

This invention is concerned with novel azacyclic derivatives, processes for their preparation, and their use in medicine, particularly as analgesics.

Compounds which are kappa-receptor agonists act as analgesics through interaction with kappa opioid receptors. The advantage of kappa-receptor agonists over the classical $\mu$-receptor agonists, such as morphine, lies in their ability to cause analgesia while being devoid of morphine-like behavioural effects and addiction liability.

European Published Application No. 232612 discloses a group of azacyclic derivatives which exhibit kappa-receptor agonism without some of the behavioural effects of morphine and morphine analogues, and which are thus of potential therapeutic utility as analgesics.

A novel class of structurally related azacyclic derivatives in which the azacyclic nucleus has at least one substituent, has now been discovered which also exhibit potent kappa-receptor agonism without the aforementioned undesirable behavioural effects.

Furthermore, this novel class of derivatives tend to show improved duration of action over corresponding unsubstituted azacyclic derivatives, while maintaining effective analgesic activity.

The novel class of derivatives also possess diuretic activity which indicates that they are of potential use in the treatment of hyponatraemic disease states in mammals.

According to the present invention there is provided a compound, or a solvate or salt thereof, of formula (I):

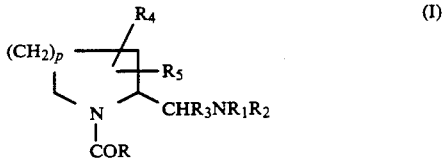

in which:

RCO is an acyl group in which the group R contains a substituted or unsubstituted carbocyclic aromatic or heterocyclic aromatic ring;

$R_1$ and $R_2$ are independently hydrogen, $C_{1-6}$ alkyl, $C_{2-6}$ alkenyl, $C_{3-6}$ cycloalkyl or $C_{4-12}$ cycloalkylalkyl groups, or together form a $C_{2-8}$ branched or linear polymethylene or $C_{2-6}$ alkenylene group, optionally substituted with a hetero-atom, $R_3$ hydrogen, $C_{1-6}$ alkyl, preferably methyl or ethyl, or phenyl, or $R_3$ together with $R_1$ form a —$(CH_2)_3$— or —$(CH_2)_4$— group;

$R_4$ and $R_5$ are independently hydrogen, hydroxyl, halogen, preferably fluorine, $C_{1-6}$ alkyl, preferably methyl or ethyl, or aryl, preferably phenyl, provided both $R_4$ and $R_5$ are not simultaneously hydrogen; and p is an integer from 1 to 4, preferably 2.

$R_4$ and $R_5$ may be located on the same or different carbon atoms of the azacyclic nucleus.

When used herein, the term 'carbocyclic aromatic group' includes single or fused rings, having 6 to 12 ring carbon atoms, and the term 'heterocyclic aromatic group' includes single or fused rings having 5 to 12 ring atoms, comprising up to four hetero-atoms in the or each ring, selected from oxygen, nitrogen and sulphur.

When the carbocyclic or heterocyclic group is a fused two ring system, one or both rings may be aromatic in character.

Suitably, one of the rings is aromatic and the other is non-aromatic.

The $C_{1-6}$ alkyl groups may be either straight or branched chain and examples are methyl, ethyl, propyl, n-butyl, n-pentyl or n-hexyl, preferably methyl.

Examples of $C_{2-6}$ alkenyl groups are 1- and 2-propenyl; an example of a $C_{3-6}$ cycloalkyl group is cyclopropyl, and an example of a $C_{4-12}$ cycloalkylalkyl group is cyclopropyl methyl.

When $R_1$ and $R_2$ together form a linear or branched polymethylene group, examples are propylene, butylene, pentylene or hexylene, preferably butylene or 1-methyl-butylene. As an alkylene group, $R_1$—$R_2$ may be typically —$CH_2$—$CH$=$CH$—$CH_2$—. Examples of hetero-atoms are oxygen and sulphur, particularly oxygen, and a suitable hetero-atom substituted polymethylene group is —$CH_2CH_2OCH_2CH_2$—.

The group R preferably has the formula (II):

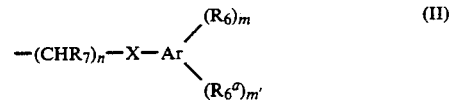

in which n is 0, 1 or 2;

m is 0, 1 or 2;

m' is 0, 1 or 2, provided m+m' $\leq$ 2

X is a direct bond, or O, S or $NR_8$ in which $R_8$ is hydrogen or $C_{1-6}$ alkyl, Ar is a substituted or unsubstituted carbocyclic or heterocyclic group, each of $R_6$ and $R_6{}^a$ is $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, optionally substituted phenyl, optionally substituted phenyl $C_{1-6}$ alkyl, hydroxy, $C_{1-6}$ alkoxy, thiol, $C_{1-6}$ alkylthio, $C_{1-6}$ haloalkoxy, $C_{1-6}$ haloalkylthio, halogen, $NO_2$, $CN$, $CF_3$, —$OCF_3$, —$OCHF_2$, —$OCF_2CF_2H$, —$OCCl_2CF_3$, —$COOR_9$, —$CONR_{10}R_{11}$, —$SO_3R_{12}$, —$SO_2NR_{13}R_{14}$ and —$COR_{15}$ in which each of $R_9$ to $R_{15}$ is independently hydrogen, $C_{1-6}$ alkyl, optionally substituted phenyl or optionally substituted phenyl $C_{1-6}$ alkyl;

or, when m is 2 and m' is 0, two $R_6$'s form a $C_{3-6}$ polymethylene group, and $R_7$ is hydrogen or $C_{1-6}$ alkyl, such as methyl or ethyl.

Preferred halogens are F, Cl and Br.

When two $R_6$'s are linked they preferably form a fused cyclopentyl or cyclohexyl ring.

Preferably Ar is phenyl and $R_6$ or $R_6{}^a$ is preferably in the meta and/or para position.

Preferably $R_6$ or $R_6{}^a$ is bromine, chlorine, or $CF_3$, particularly in the meta- or para- position.

X is typically oxygen or a direct bond, and n is typically 0 or 1.

A further preferred group R has the formula (IIa)

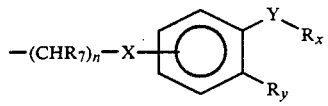

in which the group —(CHR$_7$)$_n$—X—, which is as defined in formula II, is in the meta- or para- position with respect to YR$_x$ or R$_y$, Y is >C=O, >CHOH, —S=O or —SO$_2$;

each of R$_x$ and R$_y$ is C$_{1-6}$ alkyl, or R$_x$ and R$_y$ are linked together and R$_x$ represents —(Z)$_j$— where j is 0 or 1 and Z is O, S or NR$_z$ where R$_z$ is hydrogen or C$_{1-6}$ alkyl, and R$_y$ represents —(CH$_2$)$_q$— where q is an integer of from 1 to 4, preferably 2 or 3.

A preferred sub-group of formula (IIa) is a group of formula (IIb)

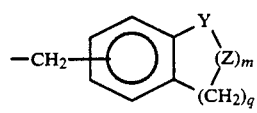

in which Y, Z, m, q and the position of —CH$_2$— are as defined in formula (IIa).

Preferably, q is 2 when Z is oxygen and m is 1, and q is 3 when m is 0.

A further preferred sub-group of formula (IIa) is the group of formula (IIc)

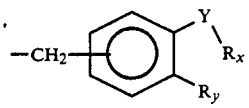

in which Y is C=O or CHOH, each of R$_x$ and R$_y$ is C$_{1-6}$ alkyl, preferably methyl, and the position of —CH$_2$— is as defined in formula (IIa)

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates.

The present invention also provides a process for the preparation of a compound of formula I which comprises reacting a compound of formula (III):

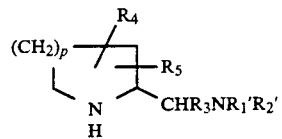

in which R$_3$, R$_4$, R$_5$ and p are as defined for formula (I), and R$_1'$ and R$_2'$ are R$_1$ and R$_2$ as defined for formula (I) or a group or atom convertible to R$_1$ and R$_2$, with a compound of formula R'CO.OH or an active derivative thereof, in which R' is R as defined for formula (I), or a group convertible to R, to form a compound of formula (Ia):

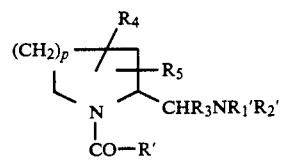

and then optionally performing one or more of the following steps:

a) where R', R$_1'$ or R$_2'$ are other than R, R$_1$ and R$_2$, converting R', R$_1'$ or R$_2'$ to R, R$_1$ or R$_2$ to obtain a compound of formula (I), b) where R', R$_1'$ and R$_2'$ are R, R$_1$ and R$_2$, converting one R, R$_1$ or R$_2$ to another R, R$_1$ or R$_2$ to obtain a compound of formula (I), c) forming a salt and/or solvate of the obtained compound of formula (I).

Suitable active derivatives of

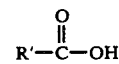

are acid chlorides or acid anhydrides. Another suitable derivative is a mixed anhydride formed between the acid and an alkyl chloroformate.

For example, in standard methods well known to those skilled in the art, the compound of formula (III) may be coupled:

a) with an acid chloride in the presence of an inorganic or organic base, b) with the acid in the presence of dicyclohexyl carbodiimide, N-dimethylaminopropyl-N'-ethyl carbodiimide or carbonyl diimidazole, c) with a mixed anhydride generated in situ from the acid and an alkyl (for example ethyl)chloroformate.

It will be appreciated that a compound of formula (Ia) may be converted to a compound of formula (I), or one compound of formula (I) may be converted to another compound of formula (I), by interconversion of suitable substituents. Thus certain compounds of formula (I) and (Ia) are useful intermediates in forming other compounds of the present invention.

R$_1'$, and R$_2'$ may be alkyl groups and converted to R$_1'$/R$_2'$ hydrogen atoms by conventional amine dealkylation. When R$_1'$ or R$_2'$ is benzyl or substituted benzyl it may be converted to an R$_1$ or R$_2$ hydrogen atom by catalytic hydrogenation or other method of reduction. $R_1'$ and $R_2'$ as hydrogen atoms may be converted to $R_1$ and $R_2$ alkyl groups by conventional amine alkylation, or by acylation followed by reduction. $R_1'$ and $R_2'$ are preferably $R_1$ and $R_2$ respectively.

The above described process will generally provide a diastereoisomeric mixture which can subsequently separated into isomers by column chromatography.

The compound

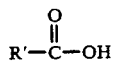

is typically of the formula (IId)

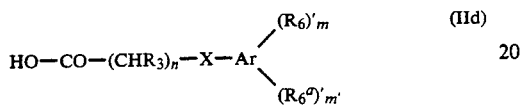

in which $R_6'$ is $R_6$ and $(R_6^a)'$ is $R_6^a$ are as defined for formula (II), or a group or atom convertible to $R_6$ or $R_6^a$, the other variables being as defined for formula (II).

Conversions of substituents $R_6'$ or $(R_6^a)'$ on the aromatic group Ar to obtain $R_6$ or $R_6^a$ are generally known in the art of aromatic chemistry. $R_6'$ is preferably $R_6$ and $(R_6^a)'$ is preferably $R_6^a$.

The compounds of formula I may be converted into their pharmaceutically acceptable acid addition salts by reaction with the appropriate organic or mineral acids. Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

As mentioned before, the compounds of formula I exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form.

Compounds of formula (III) in which $R_3$ is H may be prepared from compounds of formula (IVa) according to the following reaction Scheme 1:

Scheme 1

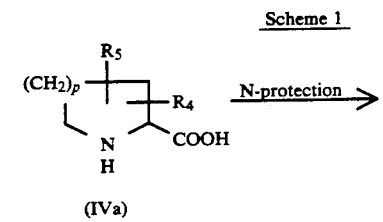

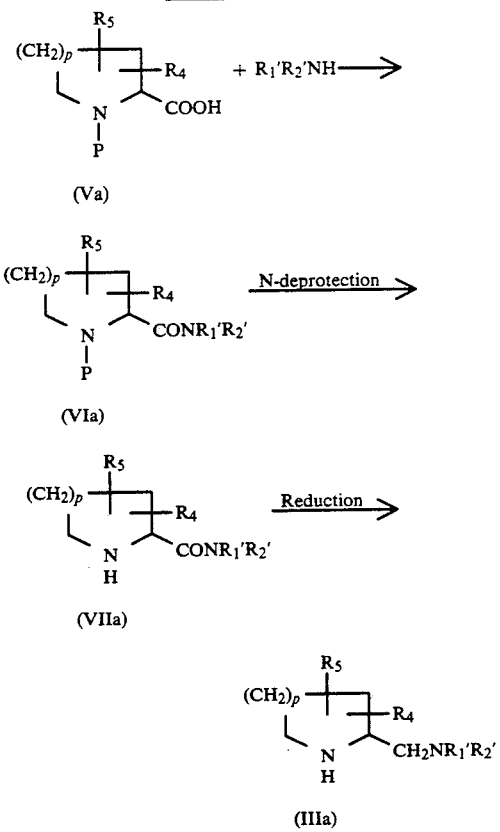

In this scheme, firstly the compound of formula (IVa) is nitrogen protected with a conventional protecting group P, such as ethoxycarbonyl or tert-butyloxycarbonyl, forming the compound of formula (Va) which is reacted with the amine $R_1'R_2'NH$ (in which $R_1'$ and $R_2'$ are as defined earlier) to obtain the N-protected amide (VIa). This is conventionally N-deprotected, and the resulting basic amide (VIIa) is reduced to the diamine (IIIa) by reaction with reducing reagents such as e.g. borane-dimethylsulphide complex or lithium aluminium hydride.

Alternatively, the N-protected acid (Va) is reduced to a primary alcohol which is converted into a reactive ester, for example with methane sulphonic acid or p-toluenesulphonic acid, and the ester reacted with $R_1'R_2'NH$. Deprotection of the ring nitrogen gives the diamine (IIIa).

Alternatively, compounds of formula (III), where $R_3=H$ and $p=2$, may be prepared from compounds of formula (IVb) according to the following reaction Scheme 2:

Scheme 2

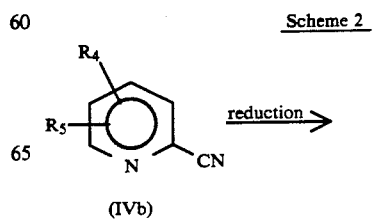

-continued
Scheme 2

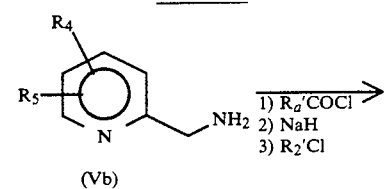
(Vb)

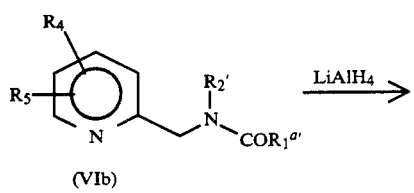
(VIb)

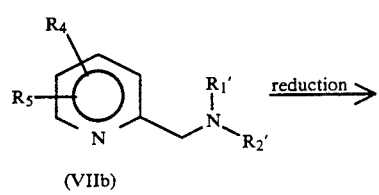
(VIIb)

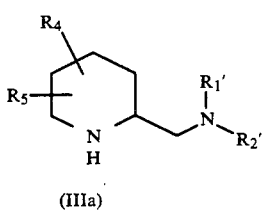
(IIIa)

In this scheme, the compound of formula (IVb) is reduced catalytically, or by means of suitable chemical reducing agents, to the corresponding aminomethylpyridine (Vb) which can be transformed into (VIb) by acylation with $R_{1a}'COCl$, where $R_{1a}'$ contains one carbon atom less than $R_1'$, and alkylation with an alkyl halide $R_2'Cl$ and a strong base (e.g. NaH), where $R_1'$ and $R_2'$ are as defined earlier.

The resulting basic amide (VIb) is reduced to the amine (VIIb) by reaction with a suitable reducing reagent e.g. lithium aluminium hydride. Finally, the reduction of the pyridine-ring of (VIIb) to give the diamine (IIIa) can be achieved by catalytic reduction using a metal such as Pt, Rh or Ru as a catalyst and acetic or trifluoroacetic acid as solvent; or by reduction with alkali metal such as sodium or potassium in alcoholic solvent.

The compounds of formula (III) in which $R_3$ is hydrogen or alkyl may also be prepared from compounds of formula (IVc) according to the following reaction Scheme 3:

Scheme 3

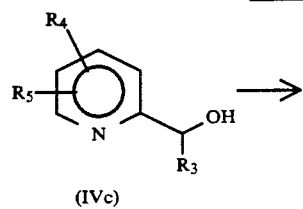
(IVc)

-continued
Scheme 3

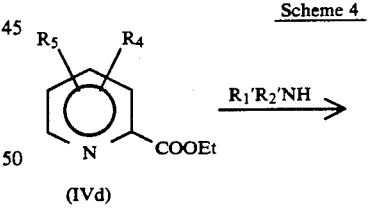
(Vc)

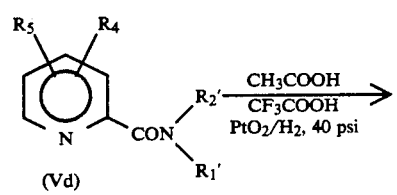
(VIc)

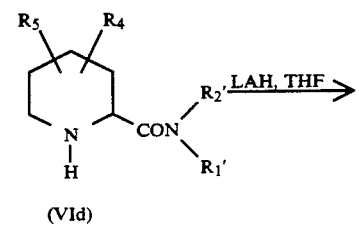
(III)

In this scheme, the compound of formula (IVc) is converted by known methods into its reactive intermediate (Vc), where X is an acyl, mesyl or tosyl derivative, or a halogen atom.

Reaction of (Vc) with the amine $R_1'R_2'NH$ (in which $R_1'$ and $R_2'$ are as defined earlier) gives the compound (VIc) which is reduced by catalytic or chemical methods, as described for Scheme 2.

Compounds of formula (III) in which $R_3$ is hydrogen and p=2 may also be prepared from compounds of formula (IVd) according to the following reaction Scheme 4. This scheme is particularly suitable for preparing compounds of formula (III) in which $R_4$ or $R_5$ is hydroxyl.

Scheme 4

-continued
Scheme 4

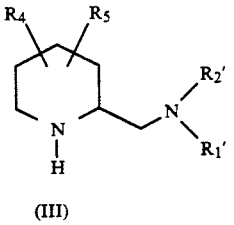

(III)

The compounds of formula (IVa), (IVb), (IVc) and (IVd) are known compounds or may be prepared by analogous procedures to known compounds. Appropriate literature references for the preparation of these compounds are as follows:

Formula (IVa): J. Med. Chem. 27, 216-223 (1984); J. Org. Chem. 50, 5032, 1985; Tetrahedron Letters 24, 5339, 1983.

Formula (IVb): J. Am. Chem. Soc. 78, 5842 (1986)

Formula (IVc): C.A. 81, 13400 (1974)

Formula (IVd): J. Het. Chem. 23, 665, 1986

The compounds of formula R'COOH are also known compounds or can be prepared from known compounds by known methods. [See, for example J.O.C. 27 (1960), 70-76; Chem. Lett. (1981), 367-370, for compounds where R' is of formula (IIa), (IIb) or IIc)].

The intermediates of formula (III) described above are novel compounds and, as such they form a further aspect of this invention.

The activity of the compounds of formula (I) in standard analgesic tests indicates that they are of potential therapeutic utility in the treatment of pain and of hyponatraemic disease states.

Accordingly the present invention also provides a compound of formula (I), or a pharmaceutically accepteble salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain, or in the manufacture of a medicament for the treatment of hyponatraemic diseases states.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents or diuretics.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain or as a diuretic.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention.

The present invention also provides a method for the treatment and/or prophylaxis of pain and/or hyponatraemic disease states in mammals, particularly humans, which comprises administering to the mammal in need of such treatment and/or prophylaxis an effective amount of a compound of formula (I) or a pharmaceutically acceptable salt or solvate thereof.

Compounds of this invention and their preparation are illustrated in the following Examples, the Descriptions illustrating the preparations of intermediates.

The compounds of the Examples are summarised in Table I.

DESCRIPTION 1

3-methyl-2-(pyrrolidin-1-yl)methyl pyridine g 14.4 (0.117 moles) of 2-hydroxymethyl-3-methyl pyridine [C.A. 81, 13400 (1974)], and ml 23 (0.164 moles) of triethylamine were dissolved in 140 ml of dry $CH_2Cl_2$. The solution obtained was cooled to $-20°$ C. and ml 13 (0.164 moles) of methanesulfonyl chloride were dropped in. The resulting solution was stirred for 2 hours at $-20°$ C. and then evaporated i.v.

The obtained solid was dissolved in 150 ml of cold methanol, and to the solution stirred and cooled at $-20°$ C., ml 25 (0.3 moles) of pyrrolidine were dropped in. The reaction mixture was stirred overnight at room temperature, evaporated i.v. and the resulting red oil dissolved in 150 ml of 10% HCl; the aqueous layer was washed with two 60 ml portions of ether, cooled at $0°$ C. and made alkaline by adding solid NaOH. The basic solution was repeatedly extracted with ether, the combined ether extracts were washed with brine, dried on $Na_2SO_4$ and evaporated in vacuo to dryness.

The oily residue was distilled at 25 mmHg b.p. $136°-139°$ C., to give 16.2 g of a slight yellow oil.

I.R. (neat) cm$-1$: 3060; 2970; 2780; 1575; 1450.

N.M.R (CDCl3) (80 MHz): δ 1.7 (m, 4H); 2.35 (s, 3H); 2.6 (m, 4H); 7.1 (dd, 1H); 7.4 (d, 1H); 8.4 (d, 1H).

DESCRIPTION 2

3-methyl-2-(pyrrolidin-1-yl)methyl piperidine g 6 (0.034 moles) of 3-methyl-2-(pyrrolidin-1-yl)methyl pyridine were dissolved in 120 ml of isoamilic alcohol and under nitrogen atmosphere, at 120° C., g 4.8 (0.21 moles) of sodium were added in small portions during 4 hours. The yellow solution obtained was kept at 120° C. for an additional hour, and then cooled and poured in 30 g of ice. The organic layer was separated and the acqueous layer was extracted twice with ether; the combined organic layer was then extracted with two 80 ml portions of HCl 37%; the acqueous layer was washed with ether and evaporated i.v. The residue was taken up in 10 ml of 40% acqueous NaOH and extracted with two 50 ml portions of ether. The combined ether extracts were then dried over anhydrous magnesium sulfate. Removal of the ether yields 3.8 g of crude product as diastereoisomeric mixture. Diast A/Diast B=72/22.4 (GLC).

I.R. (Neat): cm$-1$ 3330; 2930; 2780; 1440; 1320.

EXAMPLE 1

1-(3,4-dichlorophenyl)acetyl-2-(pyrrolidin-1-yl)methyl-3-methyl piperidine hydrochloride hemihydrate diasteroisomer A g 3.8 (0.02 moles) of 3-methyl-2-(pyrrolidin-1-yl)methyl piperidine from Description 2, dissolved in 50 ml of dry CH2Cl2, were cooled at 0° C.; to the solution obtained 5 g of $K_2CO_3$ were added and then g 5.6 (0.025 moles) of 3,4-dichlorophenylacetyl chloride were dropped in, keeping the temperature at 0° C. and under vigorous agitation. The reaction mixture was then stirred at room temperature for 12 hours, then the precipitate was filtered and the filtrate was evaporated in vacuo to dryness.

The oily residue (mixture of diastereoisomers g 8.1) was chromatographed on 100 g of silica gel, eluting with hexane containing increasing amounts of ethyl acetate (20% to 80%). The fractions collected were controlled by HPLC. The first fraction collected from the above column chromatography was found to contain diastereoisomer A almost pure, and was evaporated in vacuo to dryness. The oily compound so obtained (g 1.2) was dissolved in ethyl acetate and acidified with HCl dissolved in ether. The precipitated hydrochloride was recrystallized twice from acetone giving g 0.7 of pure diastereoisomer A, white needles, m.p. 216°–220° C.

$C_{19}H_{27}Cl_3N_2O \cdot \frac{1}{2} H_2O$: Elemental Analysis: Calcd. C, 55.01; H, 6.75; N, 6.75; Found C, 55.69; H, 6.85; N, 6.80.

I.R. (KBr): cm$-1$ 1630; 1430; 1320; 1255; 770.

N.M.R. (CDCl3) 80 MHz: δ 1.05 (d, 3H); 1.2–2.45 (m, 10H); 2.5–3.1 (m, 3H); 3.1–4.3 (m, 5H); 4 (AB system, 2H); 4.9 (dd, 1H); 7.1–7.4 (m, 3H); 11.7 (s, broad, 1H).

DESCRIPTION 3

3-methyl-2-(pyrrolidin-1-yl)methyl piperidine g 6 (0.034 moles) of 3-methyl-2-(pyrrolidin-1-yl)methyl piperidine dissolved in 150 ml of CH3COOH, plus ml 6 of CF3COOH, were hydrogenated on 200 mg of PtO2 at room temperature and 40 psi, until the theoretical amount of hydrogen was consumed. The catalyst was filtered off and the filtrate evaporated i.v. The obtained oil was taken up in 40% acqueous NaOH, and extracted with ether. The combined ethereal solutions were dried and evaporated i.v. 6 g of yellow oil were so obtained as a diastereoisomeric mixture. Diast. A/Diast. B ratio=40/60.

EXAMPLE 2

1-(3,4-dichlorophenyl)acetyl-2-(pyrrolidin-1-yl)methyl-3-methyl piperidine hydrochloride diasteroisomer B g 6 (0.033 moles) of 3-methyl-2-(pyrrolidin-1-yl)methyl piperidine from Description 3 were reacted with g 7.1 (0.035 moles) of 3,4-dichlorophenylacetyl chloride as described in Example 1. The oily residue so obtained (g 12.3) was chromatographed on 150 g of silica gel, eluting with hexane containing increasing amounts of ethyl acetate (20% to 100%).

The fractions collected were controlled by HPLC; The last fractions were found to contain diastereoisomer B almost pure, that was transformed into the hydrochloride in the same way as diastereoisomer A. The salt was crystallized firstly from acetone and then from methanol, giving g 1.2 of pure diastereoisomer B hydrochloride, as white needles, m.p. 164°–165° C.

$C_{19}H_{27}Cl_3N_2O$: Elemental Analysis: Calcd. C, 56.23; H, 6.71; N, 6.90; Found C, 56.28; H, 6.74; N, 6.93.

I.R. (KBr): cm−1 1635; 1440; 1420; 1245; 770.

N.M.R. (CDCl3) (80 MHz): δ 0.9 (d, 3H); 1.0–2.5 (m, 9H); 2.5–3.1 (m, 3H); 3.1–4.2 (m, 5H); 4 ( AB system, 2H); 5.12 (dt, 1H); 7.1–7.5 (m, 3H); 11.0 (s, broad, 1H).

DESCRIPTION 4

2-aminomethyl-4-methyl pyridine g 2 (0.0169 moles) of 2-cyano-4-methyl pyridine [J. Am. Chem. Soc. 78, 5842–5843 (1956)] dissolved in 400 ml of methanol containing 12% W/W of ammonia, were hydrogenated on 2 g of Ni-Raney at room temperature and 20 psi, until the theoretical amount of hydrogen was consumed.

The catalyst was filtered off and the filtrate evaporated in vacuo. The obtained oily product, g 1.8, was sufficiently pure for the subsequent step.

N.M.R. (CDCl3) (80 MHz): δ 2.3 (s, 3H); 3.9 (S, 2H); 7 (d, 1H); 7.1 (s, 1H); 8.4 (d, 1H).

DESCRIPTION 5

4-methyl-2-(pyrrolidin-2-one-1-yl)methyl pyridine g 3.66 (0.03 moles) of 4-methyl-2-aminomethyl pyridine were dissolved in 60 ml of dry CHCl3, ml 16.8 of triethylamine were added and the resulting solution was cooled at −20° C. g 4 (0.036 moles) of 4-chlorobutyroylchloride were then dropped in, on stirring and cooling, at such a rate to keep the temperature at −20° C.

The reaction was completed by stirring at room temperature for 2 hours, TLC CHCl3/MeOH/NH3; 94.5/5/0.5.

The reaction mixture was poured in 40 ml of 20% Na2CO3; the organic layer was separated and the aqueous layer was extracted twice with CH2Cl2. The collected organic phases were dried on Na2SO4, filtered and evaporated i.v.

The crude oil obtained was dissolved in 300 ml THF dry and under nitrogen atmosphere, at 0° C., g 1.3 of NaH 80% and ml 1 of HMPT were added. The resulting suspension was refluxed for 4 hours and then cooled and poured into 100 g of ice. The layers were separated and the aqueous layer was extracted with three 100 ml portions of ether.

The combined ethereal extracts were dried over anhydrous potassium carbonate, filtered and concentrated to dryness. The obtained oily product, g 5.4, was sufficiently pure for the subsequent step: TLC CHCl3/MeOH/NH3 86/10/0.6.

I.R. (neat): cm−1 1690; 1610; 1290.

N.M.R. (CDCl3) (80 MHz): δ 2 (t, 2H); 2.4 (S, 3H); 2.6 (t, 2H); 3.4 (t, 2H); 4.5 (s, 2H); 7.1 (m, 2H); 8.4 (d, 1H).

DESCRIPTION 6

4-methyl-2-(pyrrolidin-1-yl)methyl piperidine

By reducing g 2 of 4-methyl-2(pyrrolidin-2-one-1-yl) methyl pyridine with LiAlH4 in THF, using standard method, g 1.7 of the corresponding amine were obtained.

The compound was sufficiently pure for the following step: TLC CHCl3/MeOH/NH3 86/10/0.6.

I.R. (Neat): cm−1 2970; 2800; 1610.

g 1.7 of 4-methyl-2-(pyrrolidin-1-yl)methyl pyridine were reduced catalytically as in Description 3.

g 1.4 of slight yellow oil were obtained. The compound was sufficiently pure for the subsequent step: TLC CHCl3/MeOH/NH3 75/25/2.

I.R. (Neat): cm−1 3340; 2930; 2780; 1460; 1440.

EXAMPLE 3

1-(3,4-dichlorophenylacetyl)-2-(pyrrolidin-1-yl)methyl-4-methyl piperidine hydrochloride hemihydrate diastereoisomer A g 1.4 (0.0077 moles) of 4-methyl-2-(1-pyrrolidinyl)-methyl piperidine were reacted with g 2.1 (0.0093 moles) of 3,4-dichlorophenylacetyl chloride as described in Example 1. The oily residue so obtained (g 3.1) was chromatographed on 60 g of silica gel, eluting with CH2Cl2 containing increasing amounts of methanol (0.5 to 1.5%).

The fractions containing the pure diastereoisomer A were collected and evaporated to dryness. Only traces of diastereoisomer B were detected by TLC (86/10/0.6 CHCl3/MeOH/NH3).

The diastereoisomer A hydrochloride was precipitated from ethyl acetate and recrystallized from acetone. White needles, m.p. 199°–201° C.

$C_{19}H_{27}Cl_3N_2O \cdot \frac{1}{2} H_2O$: Elemental Analysis: Calcd. C, 55.01; H, 6.75; N, 6.75; Cl, 25.64; Found C, 55.70; H, 6.79; N, 6.74; Cl, 25.36.

I.R. (KBr): cm−1 1650; 1440; 1225.

N.M.R. (CDCl3) (80 MHz): δ 1.1 (d, 3H); 1.3–2.5 (m, 10H); 2.5–3.1 (m, 3H); 3.1–4.3 (m, 7H); 5 (m, 1H); 7.1–7.4 (m, 3H); 12 (s, broad, 1H).

DESCRIPTION 7

5-methyl-2-(pyrrolidin-1-yl)methyl piperidine

Starting from 5-methyl picolinic acid [Helv. Chem. Acta 79, 683 (1975)] 5-methyl pipecolic acid was obtained by standard method; this was transformed into N-benzyloxycarbonyl-5-methyl pipecolic acid and then into 5-methyl-2-(pyrrolidin-1-yl)carbonyl piperidine [slight yellow oil, I.R (neat) cm−1: 3450; 1640; 1420], as described in our previous patent UK 8629642 (11.12.1986, page 16–17).

By reducing g 4.5 (0.023 moles) of 5-methyl-2-(pyrrolidin-1-yl)carbonyl piperidine with LiAlH4 in THF the corresponsing diamine was obtained. The diastereoisomeric composition was checked by GLC performed on a 10 m Ph-Me silicone 50% capillary column, from 80° to 180° (rate 5°/min). Diast. A Rt 8.86 (57.93%), Diast. B. Rt 9.11 (42.07%).

I.R. (neat): cm−1 3340; 2920; 2780; 1460; 1435.

EXAMPLE 4

1-(3,4-dichlorophenylacetyl)-2-(pyrrolidin-1-yl)methyl-5-methyl piperidine hydrochloride diasteroisomer A By reaction of g 3.5 (0.19 moles) of 5-methyl-2-(pyrrolidin-1-yl)methyl piperidine with g 5.6 (0.025 moles) of 3,4-dichlorophenylacetyl chloride as described in Example 1, g 7.4 of the crude product were obtained. This was chromatographed on 80 g of silica gel (hexane-ethyl acetate), and the fractions so obtained were checked by HPLC.

The pure diastereoisomer A was obtained as hydrochloride, by crystallization from methanol, g 1.2, m.p. 218°–219° C.

$C_{19}H_{27}Cl_3N_2O$: Elemental Analysis: Calcd. C, 56.23; H, 6.71; N, 6.90; Cl, 26.21; Found C, 56.30; H, 6.74; N, 6.88; Cl, 26.26.

I.R. (KBr): cm−1 1640; 1420; 1240.

N.M.R. (CDCl3) (300 MHz): δ 0.95 (d, 3H); 1.5 (d, 2H); 1.75 (m, 1H); 2 (m, 4H); 2.2 (m, 2H); 2.7 (m, 1H); 2.85 (m, 2H); 3.6 (m, 2H); 3.8 (m, 1H); 3.95 (m, 2H); 3.8 (AB system, 2H); 5.2 (m, 1H); 7.3 (m, 3H); 11.6 (s, broad, 1H).

The last fractions were collected to give a 50/50 mixture of Diast. A and B.

DESCRIPTION 8

6-methyl-2-(pyrrolidin-1-yl)methyl pyridine

By reaction of 6-methyl-2-pyridyl methanol [prepared as described in Helv. Chim. Acta, 2429 (1957)], g 7.1 (0.058 moles), with methanesulfonyl chloride and then with pyrrolidine as in Description 1, g 7.5 of yellow oil (b.p. 62°–65° C. 80 mmHg) were obtained.

DESCRIPTION 9

6-methyl-2-(pyrrolidin-1-yl)methyl piperidine g 6 (0.034 moles) of 6-methyl-2-(pyrrolidin-1-yl)methyl pyridine were reduced as in Description 2, giving 4 g of yellow oil.

The diastereoisomeric composition was checked by a gas chromatographic analysis as in Description 7; Diastereoisomer A Rt 7.76 77%, Diastereoisomer B Rt 8.96 16%.

I.R. (neat): cm−1 3320; 2960; 2930; 2780; 1460; 1440.

EXAMPLE 5

1-(3,4-dichlorophenyl)acetyl-2-(pyrrolidin-1-yl)methyl-6-methyl piperidine hydrochloride diastereoisomer A g 4 (0.022 moles) of 6-methyl-2-(pyrrolidin-1-yl)methyl piperidine were reacted with g 6.7 (0.030 moles) of 3,4-dichlorophenylacetyl chloride as described in Example 1. The oily residue so obtained (g 10) was chromatographed on 80 g of silica gel, eluting with CHCl2 containing increasing amounts of methanol (0.5 to 1%).

The fast moving distereoisomer A was so obtained and converted into its hydrochloride salt, that was crystallized from acetone/methanol, g 3, white needles, m.p. 224°–225° C.

$C_{19}H_{27}Cl_3N_2O$: Elemental Analysis: Calcd. C, 56.23; H, 6.71; N, 6.90; Cl, 26.21; Found C, 55.93; H, 6.68; N, 6.81; Cl, 26.05.

I.R. (KBr): cm−1 1640; 1480; 1400; 1280.

N.M.R. (CDCl3) (300 MHz): δ 1.25 (d, 3H); 1.5–1.8 (m, 6H); 1.8–1.45 (m, 4H); 1.45–3 (m, 4H); 3.1–3.7 (m, 2H); 3.8 (s, 2H); 3.8–4.2 (m, 1H); 4.9 (m, 1H); 7.1–7.4 (m, 3H); 12 (s, broad, 1H).

EXAMPLE 6

1-(3,4-dichlorophenyl)acetyl-2-(pyrrolidin-1-yl)methyl-6-methyl piperidine hydrochloride hemihydrate Diastereoisomer A After separating the isomer A, elution of the column was continued using CH2Cl2 containing 1% methanol. The pure diastereoisomer B was so obtained and converted into its hydrochloride salt, that was crystallized from acetone/methanol, g 1, white needles, m.p. 156°–158° C.

$C_{19}H_{27}Cl_3N_2O \cdot \frac{1}{2} H_2O$: Elemental Analysis: Calcd. C, 55.00; H, 6.75; N, 6.75; Cl, 25.67; Found C, 55.33; H, 6.67; N, 6.75; Cl, 25.49.

I.R. (KBr): cm−1 1630; 1480; 1400; 1280.

N.M.R. (CDCl3) (300 MHz): δ 1.4 (d, 3H); 1.5–1.8 (m, 6H); 1.8–2.2 (m, 5H); 2.3–2.8 (m, 2H); 3.1-(d, 2H); 3.1–3.5 (m, 4H); 3.6 (s, 2H); 3.9 (m, 1H); 4.3 (m, 1H); 12 (s, broad, 1H).

TABLE I

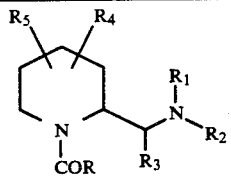

| Example | R | R1 | R2 | R3 | R4 | R5 | Diastereoisomer | Molecular formula | Melting point (0° C.) |
|---|---|---|---|---|---|---|---|---|---|
| 1 | —CH2—⟨C6H3⟩—Cl,Cl | —(CH2)4— | | H | 3Me | H | A | $C_{19}H_{27}Cl_3N_2O \cdot \frac{1}{2}H_2O$ | 216–220 |
| 2 | " | " | | " | 3Me | " | B | $C_{19}H_{27}Cl_3N_2O$ | 164–165 |
| 3 | " | " | | " | 4Me | " | A | $C_{19}H_{27}Cl_3N_2O \cdot \frac{1}{2}H_2O$ | 199–201 |
| 4 | " | " | | " | 5Me | " | A | $C_{19}H_{27}Cl_3N_2O$ | 218–219 |
| 5 | " | " | | " | 6Me | " | A | $C_{19}H_{27}Cl_3N_2O$ | 224–225 |
| 6 | " | " | | " | 6Me | " | B | $C_{19}H_{27}Cl_3N_2O \cdot \frac{1}{2}H_2O$ | 156–158 |

DESCRIPTION 10

2-(pyrrolidin-1-yl)carbonyl-3-hydroxy pyridine 18 g (0.093 moles) of ethyl-3-hydroxypicolinate [J. Heterocyclic Chem. 23, 665, 1986] were cooled at −5° C. and ml 250 of pyrrolidine were added under nitrogen atmosphere. After the addition, the solution was allowed to reach room temperature, stirred 24 h and then evaporated in vacuo to give 15 g of the title compound as a slight yellow oil which crystallized on standing.

N.M.R. (CDCl3) (80 MHz): δ 8.2–8.0 (m, 1H); 7.45–7.2 (m, 2H); 5.8 (s broad, 1H); 4.3–4.0 (m, 2H); 3.9–3.55 (m, 2H); 2.2–1.8 (m, 4H).

DESCRIPTION 11

2-(pyrrolidin-1-yl)carbonyl-3-hydroxy piperidine (diastereoisomeric amines mixture)

10 g (0.052 moles) of 2-(pyrrolidin-1-yl)carbonyl-3-hydroxy pyridine, dissolved in 100 ml of acetic acid and 8 mml of trifluoroacetic acid, were hydrogenated at 40 psi over 1 g of $PtO_2$ at room temperature, until the theoretical amount of hydrogen was consumed. The catalyst was filtered off and the filtrate evaporated in vacuo. The residue was taken up in 20% NaOH and extracted with $CH_2Cl_2$, which was dried and evaporated in vacuo to dryness. 8.5 g of the title compound were obtained as a 80/20 diastereoisomeric mixture, which was used for the subsequent step without further purification.

I.R. (neat): 3420; 2930; 1650; 1490 cm$^{-1}$

DESCRIPTION 12

2-(pyrrolidin-1-yl)methyl-3-hydroxy piperidine (diastereoisomeric diamines mixture)

By reducing 5 g (0.025 moles) of 2-(pyrrolidin-1-yl)carbonyl-3-hydroxy piperidine, with 1.2 g (0.025 moles) of $LiAlH_4$ in 100 ml of dry THF, using an alkaline work-up, 3 g of the title compound were obtained.

The compound was sufficiently pure for the following step.

EXAMPLE 7

1-(3,4-dichlorophenyl)acetyl-2-(pyrrolidin-1-yl)methyl-3-hydroxy piperidine hydrochloride diastereoisomer A trans 3.0 g (16.0 mmoles) of 2-(pyrrolidin-1-yl)methyl-3-hydroxy piperidine were reacted with g 0.89 (8.9 mmoles) of $K_2CO_3$ and 3.98 g (17.9 mmoles) of 3,4-dichlorophenylacetyl chloride as described in Example 1 with the exception of the initial temperature, kept at −20° C.

The oily residue so obtained was chromatographed on 180 g silica gel, eluting with methylene chloride containing increasing amounts of methanol (0–3.5%), to afford 0.95 g of the least polar product, which was dissolved in 10 ml of ethyl acetate and the solution brought to acidic pH with HCl/diethyl ehter.

The precipitate was filtered, washed and dried, to yield 0.065 g of the title compound. M.P.=244°–246° C.

$C_{18}H_{25}Cl_3N_2O_2$: Elemental Analysis: Calcd. C, 53.01; H, 6.17; N, 6.87; Found C, 53.60; H, 6.22; N, 6.80.

I.R. Free Base (neat): 3400; 1630; 1450; 1255 cm$^{-1}$

N.M.R. (DMSO) 300 MHz: δ 10.2 (s, broad, 1H); 7.9–6.9 (m, 3H); 5.05–4.84 (m, 1H); 4.15–2.80 (m, 10H); 2.27–1.74 (m, 10H).

EXAMPLE 8

1-(3,4-dichlorophenyl)acetyl-2-(pyrrolidin-1-yl)methyl-3-hydroxy piperidine hydrochloride diastereoisomer B cis Continuing the elution of the chromatographic column described in Example 7 with an increased amount of methanol (3.5–5%), 250 mg of the second product were obtained. This was dissolved in 40 ml of ethyl acetate and the solution brought to acidic pH with HCl/diethyl ether. The precipitate was filtered, washed ad dried, to yield 180 mg of the title compound. M.P.=259°–262° C.

$C_{18}H_{25}Cl_3N_2O_2$: Elemental Analysis: Calcd. C, 53.01; H, 6.17; N, 6.87; Found C, 53.82; H, 6.28; N, 6.80.

I.R. Free Base (KBr): 3400; 1640; 1445; 1245 cm$^{-1}$

N.M.R. (DMSO) 300 MHz: δ 10.25 (s, broad, 1H); 7.81–6.96 (m, 3H); 5.08–4.88 (m, 1H); 4.26–2.78 (m, 10H); 2.35–1.15 (m, 10H).

DESCRIPTION 13

3,3-dichloro-4,4-dimethyl-2-oxoperhydroazepine

To a stirred solution of 63.2 g (0.303 moles) of phosphorus pentachloride in 200 ml of methylene chloride at 10° C. were added 14.3 g (0.1 moles) of 3,3-dimethyl cyclohexanone oxime [Beil. 7,22–23], dissolved in 50 ml of methylene chloride and the temperature was maintained below 10° C. After the addition, the solution was allowed to reach room temperature and stirring was continued an additional 3 hours. Chlorine gas was bubbled throughout to maintain a saturated solution. The reaction was stopped by addition of chipped ice followed by saturated aqueous sodium bicarbonate. The organic layer was separated, dried over sodium sulphate and evaporated in vacuo to dryness. The residue was treated with hot n-hexane and filtered.

The solid so obtained was washed and dried, to yield 3.8 g of the title compound. M.P.=200°–202° C.

N.M.R. (CDCl3) 80 MHz: δ 7.0–6.2 (s, broad, 1H); 3.4 (m, 2H); 2.15–1.55 (m, 4H); 1.3 (ds, 6H).

DESCRIPTION 14

3-chloro-4,4-dimethyl-2-oxoperhydroazepine 3.8 g (0.018 moles) of 3,3-dichloro-4,4-dimethyl-2-oxoperhydroazepine were dissolved in 300 ml of glacial acetic acid and shaked at 40 psi of hydrogen with 1.9 g of 10% Pd/C. When the theoretical amount of hydrogen was consumed the catalyst was filtered off and the filtrate evaporated in vacuo to give 3 g of the title compound sufficiently pure for the following step.

N.M.R. (CDCl3) 80 MHz: δ 6.9–6.1 (s, broad, 1H) 4.2 (m, 1H); 3.95–3.45 (m, 1H); 3.3–2.75 (m, 1H); 2.35–1.25 (m, 4H); 1.15 (ds, 6H).

DESCRIPTION 15

3,3-dimethyl pipecolic acid

A suspension of 7.0 g (0.04 moles) of 3-chloro-4,4-dimethyl-2-oxoperhydroazepine and 13.84 g (0.043 moles) of $Ba(OH)_2 \cdot 8H_2O$ in 150 ml of water, was heated in a Parr apparatus at 150° C. for 4 hours. Then, 5.79 g (0.043 moles) of ammonium sulphate were added. The precipitate was filtered off, and the solution was evaporated in vacuo to dryness. The residue was treated with hot 2-propanol nd filtered, to yield 5 g of the title compound. M.P. >305° C.

I.R. (KBr): 3200 (broad); 3030; 1590; 1400 cm$^{-1}$

DESCRIPTION 16

1-ethoxy carbonyl-3,3-dimethyl pipecolic acid

To a stirred solution of 5 g (0.031 moles) of 3,3-dimethyl pipecolic acid and 4.44 g (0.033 moles) of potassium carbonate in 45 ml of water at 0° C., were added dropwise 3.61 g (0.033 moles) of ethyl chloroformate. After the addition was completed the solution was allowed to reach room temperature and stirring was continued for 4 hours. This solution was washed with 30 ml of methylene chloride, then brought to acidic pH with 10% HCl and extracted with methylene chloride. The organic extracts were dried and evaporated in vacuo to yield 4.4 g of the title compound.

I.R. (neat): 3250 (broad); 2950; 1740; 1680 cm$^{-1}$

DESCRIPTION 17

2-(pyrrolidin-1-yl)carbonyl-3,3-dimethyl piperidine

To a stirred solution of 5.6 g (0.026 moles) of 1-ethoxy carbonyl-3,3-dimethyl pipecolic acid in 50 ml of methylene chloride at 0° C., under nitrogen, were added 5.0 g (0.041 moles) of oxalyl chloride. After the addition the solution was allowed to reach room temperature, stirred 24 hours and evaporated in vacuo to dryness. The crude oily residue was dissolved in 30 ml of methylene chloride and added to a stirred solution of 4.44 g (0.062 moles) of pyrrolidine in 30 ml of methylene chloride at 0° C. After the addition the solution was allowed to reach room temperature and stirring was continued overnight. This solution was washed with saturated sodium bicarbonate and then with 10% HCl. The aqueous layer was brought to basic pH with 10% NaOH and extracted twice with methylene chloride. The combined extractes were dried and evaporated in vacuo to give 3.0 g of the title compound.

I.R. (neat): 3480; 2940; 1700; 1460 cm$^{-1}$

DESCRIPTION 18

2-(pyrrolidin-1-yl)methyl-3,3-dimethyl piperidine

By reducing 2.6 g (0.013 moles) of 2-(pyrrolidin-1-yl) carbonyl-3,3-dimethyl piperidine with 0.52 g (0.013 moles) of LiAlH$_4$ in 100 ml of dry THF, using an alkaline work-up, 2.0 g of the title compound were obtained. The compound was sufficiently pure for the following step.

N.M.R. (CDCl$_3$) 80 MHz: δ 3.15–2.8 (m, 1H); 2.6–2.0 (m, 8H); 1.7–1.45 (m, 5H); 1.45–1.0 (m, 4H); 0.75 (ds, 6H).

EXAMPLE 9

1-(3,4-dichlorophenyl)acetyl-2-(pyrrolidin-1-yl)methyl-3,3-dimethyl piperidine hydrochloride 1.0 g (5.49 mmoles) of 2-(pyrrolidin-1-yl)methyl-3,3-dimethyl piperidine were reacted with 0.76 g (5.76 mmoles) of K$_2$CO$_3$ and 1.28 g (5.76 mmoles) of 3,4-dichlorophenylacetyl chloride as described in Example no. 1. The oily residue so obtained was dissolved in 30 ml of ethyl acetate and the solution brought to acidic pH with HCl/diethyl ether. The precipitate was filtered, washed and dried, to yield 600 mg of the title compound. M.P. 202°–204° C.

C$_{20}$H$_{29}$Cl$_3$N$_2$O: Elemental Analysis: Calcd. C, 57.21; H, 6.96; N, 6.67; Found C, 57.11; H, 7.00; N, 6.65.

I.R. (KBr): 3430 (broad); 2960; 2550; 2460; 1680 cm$^{-1}$

N.M.R. (CDCl$_3$) 80 MHz: δ 11.8–11.2 (s, broad, 1H); 7.45–7.15 (m, 3H); 4.9–4.65 (m, 1H); 4.2–3.2 (m, 8H); 3.05–2.55 (m, 2H); 2.5–1.7 (m, 4H); 1.6–1.2 (m, 4H); 0.95 (ds, 6H).

EXAMPLE 10

1-(4-trifluoromethylphenyl)acetyl-2-(pyrrolidin-1-yl)methyl-3,3-dimethyl piperidine hydrochloride 0.8 g (4.38 mmoles) of 2-(pyrrolidin-1-yl)methyl-3,3-dimethyl piperidine were reacted with 0.43 g (4.6 mmoles) of K$_2$CO$_3$ and 1.02 g (4.6 mmoles) of 4-trifluoromethylphenylacetyl chloride as described in Example no. 1. The oily residue so obtained was dissolved in 25 ml of ethyl acetate and the solution brought to acidic pH with HCl/diethyl ether. The precipitate was filtered, washed and dried, to yield 350 mg of the title compound. M.P. 208°–210° C.

C$_{21}$H$_{30}$ClF$_3$N$_2$O: Elemental Analysis: Calcd. C,60.20; H,7.21; N,6.68; Cl,8.46; Found C,60.02; H,7.15; N,6.58; Cl,8.35.

I.R. (KBr): 3450 (broad); 3970; 2700; 2620; 2490; 1630; 1430; 1330 cm$^{-1}$

N.M.R. (CDCl$_3$) 80 MHz: δ 12.0–11.3 (s, broad, 1H); 7.7–7.4 (m, 4H); 4.95–4.65 (m, 1H); 4.3–3.1 (m, 6H); 3.05–2.50 (m, 4H); 2.5–1.75 (m, 4H); 1.5–1.15 (m, 4H); 0.90 (s, 6H).

DESCRIPTION 19

3,3-dichloro-6,6-dimethyl-2-oxoperhydroazepine

The n-hexane solution of description 13 contains a mixture 5:1 of the title compound and 3,3-dichloro-4,4-dimethyl-2-oxoperhydroazepine.

This solution was evaporated in vacuo to dryness and the residue chromatographed by flash cromatography on silica gel, eluting with a mixture 8:2 of diethyl ether and n-hexane, to yield 3.0 g of the title compound.

N.M.R. (CDCl$_3$) 80 MHz: δ 6.9–6.2 (m, 1H); 3.2–2.95 (m, 2H); 2.75–2.45 (m, 2H); 1.9–1.6 (m, 2H); 0.9 (s, 6H).

DESCRIPTION 20

3-chloro-6,6-dimethyl-2-oxoperhydroazepine 3.0 g (14.3 mmoles) of 3,3-dichloro-6,6-dimethyl-2-oxoperhydroazepine were dissolved in 300 ml of glacial acetic acid and shaked at 40 psi of hydrogen with 1.9 g of 10% Pd/C. When the theoretical amount of hydrogen was consumed the catalyst was filtered off and the filtrate evaporated in vacuo to yield 2.5 g of the title compound.

N.M.R. (CDCl$_3$) 80 MHz: δ 6.9–6.0 (m, broad, 1H); 4.65–4.45 (m, 1H); 3.5–3.15 (m, 1H); 3.0–2.5 (m, 1H); 2.25–1.2 (m, 4H); 0.9 (ds, 6H).

DESCRIPTION 21

5,5-dimethyl-pipecolic acid methyl ester hydrochloride 2.71 g (15.44 mmoles) of 3-chloro-6,6-dimethyl-2-oxoperhydro azepine were suspended in a solution of g 5.11 (17.0 mmoles) of Ba(OH)$_2$.8H$_2$O in 100 ml of water and then refluxed 2 hours. 2.14 g (17.0 mmoles) of ammonium sulphate were added. The precipitate was filtered off and the solution was evaporated in vacuo to dryness. The residue was taken up in 80 ml of methanol at 0° C. and 3.3 ml (46.32 mmoles) of thionyl chloride were added dropwise. After the addition the solution was refluxed 2 hours and evaporated in vacuo to give 2.5 g of the title compound, which was sufficiently pure for the following step. M.P.=178°–180° C.

I.R. (KBr): 3000 (broad); 1710; 1630; 1590; 1480; 1400 cm$^{-1}$

DESCRIPTION 22

2-(pyrrolidin-1-yl)carbonyl-5,5-dimethyl piperidine 4.2 g (23.5 mmoles) of 5,5-dimethyl pipecolic acid methyl ester hydrochloride were added to 40 ml of pyrrolidine kept at 0° C. After the addition, the solution was allowed to reach room temperature and stirring was continued overnight. The reaction mixture was evaporated in vacuo and the residue treated with 30 ml of 40% NaOH, extracted with diethyl ether, dried over sodium sulphate and evaporated in vacuo to dryness to give 3.3 g of the title compound.

I.R. (neat): 3480; 2940; 1680; 1450 cm$^{-1}$

DESCRIPTION 23

2-(pyrrolidin-1-yl)methyl-5,5-dimethyl piperidine

By reducing 3.3 g (15.69 mmoles) of 2-(pyrrolidin-1-yl)carbonyl-5,5-dimethyl piperidine with 0.89 g (23.5 mmoles) of LiAlH$_4$ in 80 ml of dry THF, using an alkaline work-up, 2.5 g of the title compound were obtained. The compound was sufficiently pure for the following step.

N.M.R. (CDCl$_3$) 80 MHz: δ 2.75–2.1 (m, 9H); 2.0–1.5 (m, 5H); 1.5–1.1 (m, 4H); 0.9 (ds, 6H).

EXAMPLE 11

1-(3,4-dichlorophenyl)acetyl-2-(pyrrolidin-1-yl)methyl-5,5-dimethyl piperidine hydrochloride 2.5 g (12.73 mmoles) of 2-(pyrrolidin-1-yl)methyl-5,5-dimethyl piperidine were reacted with 1.38 g (14.0 mmoles) of K$_2$CO$_3$ and 3.1 g (14.0 mmoles) of 3,4-dichlorophenyl acetyl chloride as described in Example 1.

The oily residue so obtained was dissolved in 50 ml of ethyl acetate and the solution brought to acidic pH with HCl/diethyl ether. The precipitate was filtered, washed and dried, to yield 2.5 g of the title compound. M.P. = 208°–209° C.

C$_{20}$H$_{29}$Cl$_3$N$_2$O: Elemental Analysis: Calcd. C, 57.21; H, 6.96; N, 6.67; Found C, 57.20; H, 7.03; N, 6.66.

I.R. (KBr): 3450; 2960; 2400; 1690; 1640; 1480; 1430 cm$^{-1}$

N.M.R. (CDCl$_3$) 90 MHz: δ 12.0–11.2 (s, broad, 1H); 7.55–7.3 (m, 3H); 5.45–5.1 (m, 1H); 4.4–3.1 (m, 8H); 3.1–1.1 (m, 10H); 0.9 (ds, 6H).

EXAMPLE 12

1-(5,6,7,8-tetrahydronapht-2-yl)acetyl-2-(pyrrolidin-1-yl) methyl-3,3-dimethyl piperidine hydrochloride To a stirred solution of 0.7 g (3.84 mmoles) of 2-(pyrrolidin-1-yl)methyl-3,3-dimethyl piperidine and 0.87 g (4.6 mmoles) of 5,6,7,8-tetrahydronapht-2-yl acetic acid in dry CHCl$_3$ at −10° C., were added 1.43 g (6.97 mmoles) of DCC dissolved in 10 ml of dry CHCl$_3$. After the addition, the solution was allowed to reach room temperature and stirring was continued overnight. The precipitate was filtered off and the filtrate was evaporated in vacuo. The residue was dissolved in 30 ml of ethyl acetate and washed with 10% NaOH. The organic layer was dried over sodium sulphate and evaporated in vacuo.

The oily residue was taken up in 30 ml of ethyl acetate and brought to acidic pH with HCl/diethyl ether. The precipitate was filtered, washed and dried, to yield 550 mg of the title compound. M.P. = 197°–199° C.

C$_{24}$H$_{37}$ClN$_2$O: Elemental analysis: Calcd. C,71.17; H,9.20; N,6.91; Cl,8.75; Found C,71.02; H,9.09; N,6.88; Cl,8.74.

I.R. (KBr): 3420 (broad); 2930; 2700; 1670; 1460 cm$^{-1}$

N.M.R. (CDCl$_3$) 80 MHz: δ 11.7–10.8 (s, broad, 1H); 7.05–6.85 (m, 3H); 4.95–4.60 (m, 1H); 4.20–3.05 (m, 6H); 3.0–2.4 (m, 8H); 2.4–1.45 (m, 8H); 1.40–1.0 (m, 4H); 0.9 (s, 6H)

EXAMPLE 13

1-[1-oxo-3,4-dihydro-(2H)-napht-6-yl]acetyl-2-(pyrrolidin-1-yl)methyl-3,3-dimethyl piperidine 300 mg (1.65 mmoles) of 2-(pyrrolidin-1-yl)methyl-3,3-dimethylpiperidine were reacted with 273 mg (1.78 mmoles) of K$_2$CO$_3$ and 441 mg (1.98 mmoles) of 1-oxo-3,4-dihydro-(2H)-napht-6-yl acetyl chloride as described in Example No. 1. The oily residue was chromatographed by flash cromatography on silica gel, eluting with a mixture 94.5:5:0.5 of CH$_2$Cl$_2$/MeOH/conc. NH$_4$OH, to yield 150 mg of the title compound as a viscous oil.

C$_{24}$H$_{34}$N$_2$O$_2$

I.R. (Neat): 2960; 2875; 2780; 1685; 1640; 1610; 1450 cm$^{-1}$

N.M.R. (CDCl$_3$) 80 MHz: δ 7.9–7.0 (m, 3H); 4.7–4.35 (m, 1H); 3.85–3.6 (m, 5H); 3.6–1.9 (m, 9H); 1.9–1.0 (m, 10H) 0.9 (ds, 6H).

DESCRIPTION 24

3,3-dichloro-5,5-dimethyl-2-oxoperhydroazepine 23.7 g (0.167 moles) of 4,4-dimethyl cyclohexanone oxime [Beil. 7,I,17] and 104.8 g (0.503 moles) of phosphorus pentachloride in 300 ml of CH$_2$Cl$_2$ were reacted as in Description 13 to yield 15.2 g of the title compound.

M.P. = 108°–110° C.

N.M.R (CDCl$_3$) 80 MHz: δ 7.0–6.5 (s, broad, 1H); 3.55–3.20 (m, 2H); 2.55 (s, 2H); 1.7–1.35 (m, 2H); 1.1 (s, 6H).

DESCRIPTION 25

3-chloro-5,5-dimethyl-2-oxoperhydroazepine 15.2 g (0.086 moles) of 3,3-dichloro-5,5-dimethyl-2-oxoperhydroazepine were dissolved in 900 ml of glacial acetic acid and shaked at 40 psi of hydrogen with 7 g of 10% Pd/C as in Description 14, to yield 13.6 g of the title compound.

M.P. = 100°–103° C.

N.M.R. (CDCl$_3$) 80 MHz: δ 7.5–6.8 (m, broad, 1H); 4.85–4.5 (m, 1H); 3.4–3.05 (m, 2H); 2.0–1.85 (m, 2H); 1.6–1.3 (m, 2H); 1.05 (ds, 6H).

DESCRIPTION 26

4,4-dimethyl pipecolic acid methyl ester hydrochloride

A suspension of 9.6 g (0.054 moles) of 3-chloro-5,5-dimethyl-2-oxoperhydroazepine and 18.98 g (0.054 moles) of Ba(OH)$_2$.8H$_2$O in 250 ml of water, was heated in a Parr apparatus at 110° C. for 2 hours. Then, 7.22 g (0.054 moles) of ammonium sulphate were added. The precipitate was filtered off, and the solution was evaporated in vacuo to dryness. The residue was treated with hot 2-propanol and filtered to afford a white solid which was dissolved in water and passed over an ion-exchange column (Dovex 50). The residual salts were removed with 200 ml of water and the aminoacid was eluted with 2N ammonium hydroxide to yield 6.0 g of 4,4-dimethyl pipecolic acid. M.P. >300° C. (dec.).

The aminoacid was taken up in 150 ml of methanol at 0° C. and 8.25 ml (0.11 moles) of thionyl chloride were added dropwise. After the addition the solution was refluxed two hours and evaporated in vacuo to give 7.3 g of the title compound, which was sufficiently pure for the following step. M.P. >305° C..

I.R. (KBr): 3000 (broad); 1750; 1570; 1400; 1370 cm$^{-1}$

DESCRIPTION 27

2-(pyrrolidin-1-yl)carbonyl-4,4-dimethyl piperidine 5 g (0.024 moles) of 4,4-dimethyl pipecolic acid methyl ester hydrochloride were reacted with 100 ml of pyrrolidine as described in Description 22 to yield 5.4 g of the title compound.

I.R. (Neat): 3450; 2950; 1685; 1415 cm$^{-1}$

DESCRIPTION 28

2-(pyrrolidin-1-yl)methyl-4,4-dimethyl piperidine

By reducing 5.4 g (0.027 moles) of 2-(pyrrolidin-1-yl)carbonyl-4,4-dimethyl piperidine with 1.1 g (0.027 moles) of LiAlH$_4$ in 100 ml of dry THF, using an alkaline work-up, 3.8 g of the title compound were obtained.

I.R. (Neat): 3330; 2960; 2790; 1520; 1450 cm$^{-1}$

EXAMPLE 14

1-(3,4-dichlorophenyl)acetyl-2-(pyrrolidin-1-yl)methyl-4,4-dimethyl piperidine hydrochloride 1 g (5.09 mmoles) of 2-(pyrrolidin-1-yl)methyl-4,4-dimethyl piperidine were reacted with 0.55 g (5.6 mmoles) of K$_2$CO$_3$ and 1.24 g (5.6 mmoles) of 3,4-dichlorophenylacetyl chloride as described in Example No. 1.

The oily residue was dissolved in 25 ml of ethyl acetate and 5 ml of acetone. This solution was brought to acidic pH with HCl/ethyl ether. The precipitate was filtered, washed and dried, to yield 1.0 g of the title compound. M.P.=171°–172° C.

C$_{20}$H$_{29}$Cl$_3$N$_2$O: Elemental analysis: Calcd. C,57.21; H,6.96; N,6.67; Cl,25.30; Found C,57.34; H,7.00; N,6.69; Cl,25.14.

I.R. (KBr): 3440 (broad); 2960; 2640; 2480; 1625: 1475 cm$^{-1}$

N.M.R. (CDCl$_3$) 80 MHz: δ 11.9–11.2 (s, broad, 1H); 7.35–7.05 (m, 3H); 5.2–4.9 (m, 1H); 4.25–3.2 (m, 6H); 3.1–2.4 (m, 4H); 2.35–1.75 (m, 4H); 1.7–1.1 (m, 4H); 0.95 (ds, 6H).

EXAMPLE 15

1-(4-trifluoromethylphenyl)acetyl-2-(pyrrolidin-1-yl)methyl-4,4-dimethyl piperidine hydrochloride 1 g (5.09 mmoles) of 2-(pyrrolidin-1-yl)methyl-4,4-dimethyl piperidine were reacted with 0.55 g (5.6 mmoles) of K$_2$CO$_3$ and 1.24 g (5.6 mmoles) of 4-trifluoromethylphenyl acetyl chloride as described in Example No. 1.

The oily residue was dissolved in 25 ml of ethyl acetate and 5 ml of acetone. This solution was brought to acidic pH with HCl/ethyl ether. The precipitate was filtered, washed and dried, to yield 1.3 g of the title compound. M.P.=174°–175° C.

C$_{21}$H$_{30}$ClF$_3$N$_2$O: Elemental analysis: Calcd. C,60.20; H,7.21; N,6.68; Cl,8.46; Found C,60.28; H,7.24; N,6.67; Cl,8.48.

I.R. (KBr): 3450 (broad); 2920: 2600; 2480; 1630; 1360 cm$^{-1}$

N.M.R. (CDCl$_3$) 80 MHz: δ 12.0–11.3 (s, broad, 1H); 7.7–7.3 (m, 4H); 5.25–4.9 (m, 1H); 4.4–3.2 (m, 6H); 3.0–2.5 (m, 4H); 2.4–1.8 (m, 4H); 1.7–1.2 (m, 4H); 0.9 (ds, 6H).

TABLE I (continued)

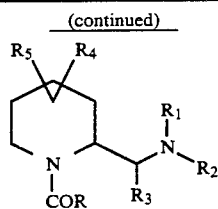

| Example | R | R$_1$ R$_2$ | R$_3$ | R$_4$ | R$_5$ | Diastereoisomer | Molecular formula | Melting Point (°C.) |
|---|---|---|---|---|---|---|---|---|
| 7 | —CH$_2$—C$_6$H$_3$Cl$_2$ (3,4-diCl) | —(CH$_2$)$_4$— | H | 3OH | H | A TRANS | C$_{18}$H$_{25}$Cl$_3$N$_2$O$_2$ | 244–246 |
| 8 | " | —(CH$_2$)$_4$— | H | 3OH | H | B CIS | C$_{18}$H$_{25}$Cl$_3$N$_2$O$_2$ | 259–262 |
| 9 | " | —(CH$_2$)$_4$— | H | 3CH$_3$ | 3CH$_3$ | | C$_{20}$H$_{29}$Cl$_3$N$_2$O | 202–204 |
| 10 | —CH$_2$—C$_6$H$_4$—CF$_3$ | —(CH$_2$)$_4$— | H | 3CH$_3$ | 3CH$_3$ | | C$_{21}$H$_{30}$ClF$_3$N$_2$O | 208–210 |
| 11 | —CH$_2$—C$_6$H$_3$Cl$_2$ | —(CH$_2$)$_4$— | H | 5CH$_3$ | 5CH$_3$ | | C$_{20}$H$_{29}$Cl$_3$N$_2$O | 208–209 |

TABLE I-continued (continued)

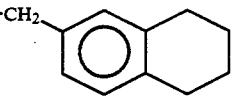

| Example | R | $R_1$ $R_2$ | $R_3$ | $R_4$ | $R_5$ | Diastereoisomer | Molecular formula | Melting Point (°C.) |
|---------|---|-------------|-------|-------|-------|-----------------|-------------------|---------------------|
| 12 | 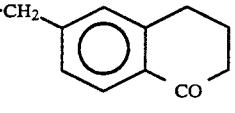 | $-(CH_2)_4-$ | H | $3CH_3$ | $3CH_3$ | | $C_{24}H_{37}ClN_2O$ | 197–199 |
| 13 | 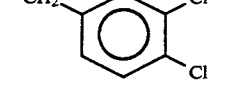 | $-(CH_2)_4-$ | H | $3CH_3$ | $3CH_3$ | | $C_{24}H_{34}N_2O_2$ | — |
| 14 | 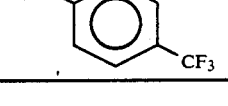 | $-(CH_2)_4-$ | H | $4CH_3$ | $4CH_3$ | | $C_{20}H_{29}Cl_3N_2O$ | 171–172 |
| 15 |  | $-(CH_2)_4-$ | H | $4CH_3$ | $4CH_3$ | | $C_{21}H_{30}ClF_3N_2O$ | 174–175 |

EXAMPLE 16

(−)-1-(4-trifluoromethylphenyl)acetyl-2-(pyrrolidin-1-yl) methyl-3,3-dimethyl piperidine hydrochloride 2.3 g (6.01 mmoles) of the free base of the compound of Ex. No. 10 were dissolved in 35 ml of abs. ethanol. 2.55 g (6.31 mmoles) of (+)-di-O,O'-p-toluoyl-D-tartaric acid, dissolved in 35 ml of ethanol, were added to the hot solution of the free base.

After a gentle warming the solution was filtered and the less soluble diastereomeric salt crystallized on standing. The salt was recrystallized from abs. ethanol, up to a constant rotatory power, to give 1.2 g of (+)-di-O-O'-p-toluoyl-D-tartrate.

M.P.=170°–172° C.
$[\alpha]_D^{20}= +39.10$ (C=1, MeOH)

The tartrate salt was transformed into the free base by dissolving in acq. $NH_3$ solution, extracting with diethyl ether and evaporating the solvent in vacuo. The obtained free base was dissolved in 20 ml of ethyl acetate and the solution was brought to acidic pH with HCl/diethyl ether. The precipitate was filtered, washed and dried to yield 550 mg of the title compound.

$C_{21}H_{30}ClF_3N_2O$
M.P.=161°–163° C.
$[\alpha]_D^{20}= -49.79$ (C=1, MeOH)

The I.R. and N.M.R. spectra were identical to those obtained for the racemate.

EXAMPLE 17

(+)-1-(4-trifluoromethylphenyl)acetyl-2-(pyrrolidin-1-yl)methyl-3,3-dimethyl piperidine hydrochloride The mother liquors of the first crystallization of Ex. No. 16 were evaporated in vacuo to dryness. The residue was treated with acq. $NH_3$ solution and extracted with diethyl ether to afford 1.4 g (3.66 mmoles) of the enriched free base, which was dissolved in 40 ml of abs. ethanol. 1.54 g (3.80 mmoles) of (−)-di-O,O'-p-toluoyl-L-tartaric acid, dissolved in abs. ethanol, were added to the warm solution and the diastereoisomeric salt crystallized on standing. The salt was recrystallized from abs. ethanol, up to a constant rotatory power, to give 1.05 g of (−)-di-O,O'-p-toluoyl-L-tartrate.

M.P.=171°–173° C.
$[\alpha]_D^{20}= -38.38$ (C=1, MeOH)

The tartrate salt was transformed into the free base by dissolving in acq. $NH_3$ solution, extracting with diethyl ether and evaporating the solvent in vacuo. The obtained free base was dissolved in 20 ml of ethyl acetate and the solution was brought to acidic pH with HCl/diethyl ether. The precipitate was filtered, washed and dried to yield 400 mg of the title compound.

$C_{21}H_{30}ClF_3N_2O$
M.P.=161°–163° C.
$[\alpha]_D^{20}= +50.98$ (C=1, MeOH)

The I.R. and N.M.R. spectra were identical to those obtained for the racemate.

TABLE I (continued)

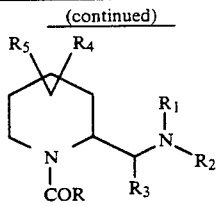

| Example | R | R₁ R₂ | R₃ | R₄ | R₅ | Molecular formula | Melting Point (°C.) | $[\alpha]_D^{20}$ (C = 1, MeOH) |
|---|---|---|---|---|---|---|---|---|
| 16 | CH₂—⟨⟩—CF₃ | —(CH₂)₄— | H | 3CH₃ | 3CH₃ | $C_{21}H_{30}ClF_3N_2O$ | 161–163 | −49.79 |
| 17 | CH₂—⟨⟩—CF₃ | —(CH₂)₄— | H | 3CH₃ | 3CH₃ | $C_{21}H_{30}ClF_3N_2O$ | 161–163 | +50.98 |

The pharmacological activity of the compounds of this invention is illustrated by various in vitro and in vivo models, using the following test procedures, in which the mousetail flick test demonstrates analgesic activity.

PHARMACOLOGICAL TESTS

A) P-phenylquinone-induced abdominal writhing test in mice

The methodology employed is based on that described by Sigmund et al, Proc. Soc. Exptl. Biol. 95, 729/1957, modified by Milne and Twomey, Agents and Actions, 10, 31/1980.

Male Charles River mice (Swiss Strain), 25–36 g body weight, were used. Animals were allowed food and water ad libitum and were randomized into groups of 10 prior to experimentation. Test compounds were dissolved in either distilled water or distilled water plus 0.1M AMS, and administered by the subcutaneous route in a final volume of 10 ml/Kg. Control animals received 10 ml/Kg of the appropriate vehicle alone. Following a pretreatment period of 20 min., mice were injected intraperitoneally with p-phenylquinone, 2 mg/Kg at 37° C. in a final volume of 10 mg/Kg. Next, the mice were placed, in groups of 3, in a compartmented perspex box maintained at room temperature and were observed for a period of 8 min. During this period the number of abdominal writhing responses per animal were recorded where writhing consists of an intermittent contraction of the abdomen associated with hind leg extension.

The degree of antinociceptive protection afforded by the test compound was determined as the mean number of writhing responses observed in the treated group (T) expressed as a percentage of the mean number of writhing responses in the control group (C) according to the following formula:

$$[1-(T/C)] \times 100\% \text{ graded protection}$$

B) Tail-flick test in mice

The methodology employed is based on that described by D'Amour and Smith, J. Pharmacol. Exp. Ther. 72, 74/1941.

Male Charles River mice (Swiss Strain), 22–34 g body weight were used. Animals were allowed food and water ad libitum and were randomized into groups of 10 prior to experimentation. Before administration of the test compound, the reaction time of each animal was determined by focusing a beam of light onto the tail, eliciting a reflex withdrawal after a certain latency; only mice exhibiting a latency between 3–8 sec. were used subsequently in the evaluation of drug effects.

Test compounds were dissolved in either distilled water or distilled water plus 0.1M AMS and administered by the subcutaneous route in a final volume of 10 ml/Kg. Control animals received 10 ml/kg of the appropriate vehicle alone. Following a pretreatment period of 30 min., the mice were again placed under the heat source and the reaction tine re-determined.

Percentage quantal protection was determined as the number of mice in which the reaction time was doubled compared to pretreatment values, expressed as a percentage of the total number of mice in the group. The results are summarised in Table (II)

TABLE II

| | PHARMACOLOGICAL DATA | | | |
|---|---|---|---|---|
| | ANALGESIA | | DURATION OF ACTION | |
| | M. WRITHING (GRADED) ED50 mg/ | M. TAIL-FLICK (QUANTAL) ED50 mg/ | M. TAIL-FLICK (GRADED) % ACTIVITY AT MTFQ ED50 | |
| Example | Kg sc | Kg sc | 30' | 90' |
| 1 | 0.093 (0.076–0.113) | 0.405 (0.230–0.607) | 87 | 68 |
| 2 | 0.091 (0.075–0.112) | 0.147 (0.091–0.237) | 66 | 44 |
| 3 | 0.149 (0.104–0.212) | 0.202 (0.135–0.303) | 86 | 17 |
| 4 | 0.163 (0.123–0.217) | 0.749 (0.448–1.252) | 80 | 54 |
| 5 | 0.030 (0.019–0.047) | 0.135 (0.083–0.221) | 83 | 42 |
| 6 | — | (1.78 mg/Kg 60%) | 77 | 35 |
| 7 | 0.141 (0.128–0.156) | 0.825 (0.493–1.378) | 87 | 39 |
| 8 | — | at 10 mg = 20% protection | | |
| 9 | 0.029 (0.023–0.036) | 0.136 (0.060–0.304) | 86 | 58 |

TABLE II-continued
PHARMACOLOGICAL DATA

| | ANALGESIA | | DURATION OF ACTION | |
|---|---|---|---|---|
| Example | M. WRITHING (GRADED) ED50 mg/Kg sc | M. TAIL-FLICK (QUANTAL) ED50 mg/Kg sc | M. TAIL-FLICK (GRADED) % ACTIVITY AT MTFQ ED50 | |
| | | | 30' | 90' |
| 10 | 0.023 (0.19–0.028) | 0.116 (0.078–0.174) | 59 | 57 |
| 11 | 0.605 (0.493–0.741) | 1.163 (0.776–1.743) | 59 | 57 |
| 12 | 0.273 (0.159–0.465) | 1.212 (0.726–2.027) | 67 | 65 |
| 13 | — | at 10 mg = 60% protection | | |
| 14 | 0.147 (0.114–0.191) | 0.824 (0.512–1.326) | 69 | 69 |
| 15 | 0.242 (0.179–0.329) | 1.797 (1.075–3.002) | 58 | 63 |

We claim:

1. A compound of the formula

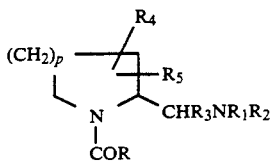

or a solvate or salt thereof wherein $R_1$ and $R_2$ are independently hydrogen, alkyl of 1 to 6 carbon atoms, alkenyl of 2 to 6 carbon atoms, cycloalkyl of 3 to 6 carbon atoms or cycloalkylalkyl of 4 to 12 carbon atoms, or $R_1$ and $R_2$ together form a branched or linear polymethylene of 2 to 8 carbon atoms or alkenylene of 2 to 6 carbon atoms, optionally including a hetero-atom selected from the group consisting of oxygen and sulphur, $R_3$ is hydrogen, alkyl of 1 to 6 carbon atoms or phenyl, or $R_3$ together with $R_1$ form $-(CH_2)_3-$ or $-(CH_2)_4-$;

$R_4$ and $R_5$ are independently hydrogen, hydroxyl, halogen, alkyl of 1 to 6 carbon atoms, provided both $R_4$ and $R_5$ are not simultaneously hydrogen;

p is 2; and

R is a moiety of the formula (II):

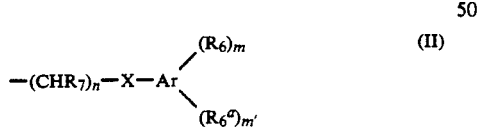

in which n is 0, 1 or 2;

m is 0, 1 or 2; and m' is 0, 1 or 2, provided m+m'≦2;

X is a direct bond, O, S or $NR_8$ in which $R_8$ is hydrogen or alkyl of 1 to 6 carbon atoms, Ar is phenyl, each of $R_6$ and $R_6{}^a$ is alkyl of 1 to 6 carbon atoms, alkenyl of 2 to 6 carbon atoms, alkynyl of 2 to 6 carbon atoms, haloalkyl of 1 to 6 carbon atoms, haloalkenyl of 2 to 6 carbon atoms, haloalkynyl of 2 to 6 carbon atoms, phenyl, phenylalkyl of 1 to 6 carbon atoms in the alkyl moiety, hydroxy, alkoxy of 1 to 6 carbon atoms, thiol, alkylthio of 1 to 6 carbon atoms, haloalkoxy of 1 to 6 carbon atoms, haloalkylthio of 1 to 6 carbon atoms, halogen, $NO_2$, CN, $CF_3$, $-OCF_3$, $-OCHF_2$, $-OCF_2CF_2H$, $-OCCl_2CF_3$, $-COOR_9$, $-CONR_{10}R_{11}$, $-SO_3R_{12}$, $-SO_2NR_{13}R_{14}$ or $-COR_{15}$ in which each of $R_9$ to $R_{15}$ is independently hydrogen, alkyl of 1 to 6 carbon atoms, phenyl or phenylalkyl of 1 to 6 carbon atoms in the alkyl moiety;

or, when m is 2 and m' is 0, two $R_6$'s together form polymethylene of 3 to 6 carbon atoms, and $R_7$ is hydrogen or alkyl of 1 to 6 carbon atoms.

2. A compound of the formula (I):

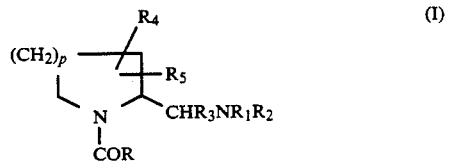

or a solvate or salt thereof wherein $R_1$ and $R_2$ are independently hydrogen, alkyl of 1 to 6 carbon atoms, alkenyl of 2 to 6 carbon atoms, cycloalkyl of 3 to 6 carbon atoms or cycloalkylalkyl of 4 to 12 carbon atoms in each alkyl moiety, or together form a branched or linear polymethylene of 2 to 8 carbon atoms or alkenylene of 2 to 6 carbon atoms optionally including a hetero-atom selected from the group consisting of oxygen and sulphur, $R_3$ is hydrogen, alkyl of 1 to 6 carbon atoms or phenyl, or $R_5$ together with $R_1$ form $-(CH_2)_3-$ or $-(CH_2)_4-$;

$R_4$ and $R_5$ are independently hydrogen, hydroxyl, halogen, alkyl of 1 to 6 carbon atoms, provided both $R_4$ and $R_5$ are not simultaneously hydrogen;

p is 2; and

R is a moiety of the formula (IIa)

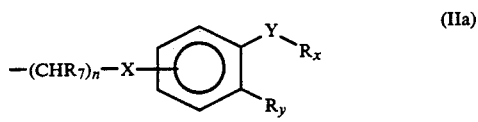

in which $-(CHR_7)_{11}-X-$ is in the meta- or para- position with respect to $YR_x$ or $R_y$, n is 0, 1 or 2, X is a direct bond or O, S, or $NR_5$, wherein $R_5$ is hydrogen or $C_{1-6}$ alkyl;

Y is $>C=O$, $>CHOH$, $-S=O$ or $-SO_2$;

each of $R_x$ and $R_y$ is alkyl of 1 to 6 carbon atoms, or $R_x$ and $R_y$ are linked together and $R_z$ is $-(Z)j-$ wherein j is 0 or 1 and Z is O, S or $NR_x$ wherein $R_x$ is hydrogen or alkyl of 1 to 6 carbon atoms, and $R_y$ is $-(CH_2)_q-$ where q is an integer of from 1 to 4.

3. A compound according to claim 1 or 2, in which each of $R_1$ and $R_2$ methyl, ethyl, propyl, butyl, pentyl or hexyl.

4. A compound according to claim 1 or 2, in which $R_1$ and $R_2$ together form propylene, butylene, pentylene, hexylene, or $-CH_2-CH=CH-CH_2-$.

5. A compound selected from the group consisting of:

1-(3,4-dichlorophenyl)acetyl-2-(pyrrolidin-1-yl)methyl-3-methyl piperidine;

1-(3,4-dichlorophenyl)acetyl-2-(pyrrolidin-1-yl)methyl-4-methyl piperidine;

1-(3,4-dichlorophenyl)acetyl-2-(pyrrolidin-1-yl)methyl-5-methyl piperidine;

1-(3,4-dichlorophenyl)acetyl-2-(pyrrolidin-1-yl)methyl-6-methyl piperidine;

1-(3,4-dichlorophenyl)acetyl-2-(pyrrolidin-1-yl)methyl-3-hydroxy piperidine;

1-(3,4-dichlorophenyl)acetyl-2-(pyrrolidin-1-yl)methyl-3,3-dimethyl piperidine;

1-(4-trifluoromethylphenyl)acetyl-2-(pyrrolidin-1-yl)methyl-3,3-dimethyl piperidine;

1-(3,4-dichloromethylphenyl)acetyl-2-(pyrrolidin-1-yl)methyl-5,5-dimethyl piperidine;

1-(5,6,7,8-tetrahydronaphth-2-yl)acetyl-2-(pyrrolidin-1-yl)methyl-3,3-dimethyl piperidine;

1-[1-oxo-3,4-dihydro-(2H)-naphth-6-yl]acetyl-2-(pyrrolidin-1-yl)methyl-3,3-dimethyl piperidine;

1-(3,4-dichlorophenyl)acetyl-2-(pyrrolidin-1-yl)methyl-4,4-dimethyl piperidine;

1-(4-trifluoromethylphenyl)acetyl-2-(pyrrolidin-1-yl)methyl-4,4-dimethyl piperidine;

(−)-1-(4-trifluoromethylphenyl)acetyl-2-(pyrrolidin-1-yl)methyl-3,3-dimethyl piperidine;

(+)-1-(4-trifluoromethylphenyl)acetyl-2-(pyrrolidin-1-yl)methyl-3,3-dimethyl piperidine.

6. A pharmaceutical composition for the treatment and/or prophylaxis of pain in mammals, comprising an effective amount of a compound of formula (I), as defined in claim 1 or 2, or a salt or solvate thereof, and a pharmaceutically acceptable carrier.

7. A method for the treatment and/or prophylaxis of pain in mammals, which comprises administering to the mammal in need of such treatment and/or prophylaxis an effective amount of a compound of formula (I), as defined in claim 1 or 2, or a salt or solvate thereof.

* * * * *